(12) United States Patent
Steinbach et al.

(10) Patent No.: US 8,231,598 B2
(45) Date of Patent: Jul. 31, 2012

(54) PROPELLANT BAG IMPROVEMENT

(75) Inventors: Bernd Steinbach, Friedberg (DE); Falko Bitz, Mainz (DE)

(73) Assignee: Palyon Medical (BVI) Limited (VG)

( * ) Notice: Subject to any disclaimer, the term of this patent is extended or adjusted under 35 U.S.C. 154(b) by 90 days.

(21) Appl. No.: 12/609,385

(22) Filed: Oct. 30, 2009

(65) Prior Publication Data

US 2011/0106010 A1   May 5, 2011

(51) Int. Cl.
*A61M 5/32* (2006.01)

(52) U.S. Cl. ........... 604/415; 604/403; 604/408; 222/92

(58) Field of Classification Search .................. 604/405, 604/415, 416, 905, 140, 141, 403, 408; 222/92; 141/20
See application file for complete search history.

(56) References Cited

U.S. PATENT DOCUMENTS

| | | | |
|---|---|---|---|
| 4,698,061 A * | 10/1987 | Makaryk et al. .............. 604/408 |
| 4,969,873 A | 11/1990 | Steinbach et al. |
| 5,085,656 A | 2/1992 | Polaschegg |
| 5,277,336 A * | 1/1994 | Youel ............................ 222/105 |
| 5,336,194 A | 8/1994 | Polaschegg et al. |
| 5,611,792 A * | 3/1997 | Gustafsson ................... 604/403 |
| 5,722,957 A | 3/1998 | Steinbach |
| 5,766,150 A | 6/1998 | Langkau |
| 5,814,019 A | 9/1998 | Steinbach et al. |
| 5,836,915 A | 11/1998 | Steinbach et al. |
| 6,730,060 B1 | 5/2004 | Steinbach et al. |
| 6,994,699 B2 * | 2/2006 | Houwaert et al. ............. 604/408 |
| 7,025,754 B2 * | 4/2006 | Proicou et al. ................ 604/408 |
| 7,637,892 B2 | 12/2009 | Steinbach et al. |
| 7,708,730 B2 | 5/2010 | Steinbach et al. |
| 2006/0259015 A1 | 11/2006 | Steinbach |
| 2006/0259016 A1 | 11/2006 | Steinbach |
| 2006/0271021 A1 | 11/2006 | Steinbach |
| 2006/0271022 A1 | 11/2006 | Steinbach et al. |
| 2007/0005044 A1 | 1/2007 | Steinbach et al. |
| 2007/0112328 A1 | 5/2007 | Steinbach et al. |
| 2010/0069892 A1 | 3/2010 | Steinbach et al. |

OTHER PUBLICATIONS

U.S. Appl. No. 12/715,837.

* cited by examiner

*Primary Examiner* — Laura Bouchelle

(74) *Attorney, Agent, or Firm* — Lerner, David, Littenberg, Krumholz & Mentlik, LLP

(57) ABSTRACT

An improved propellant pillow and method for filling a propellant chamber of an implantable pump with propellant through the use of such an improved propellant pillow are disclosed. The propellant pillow includes an improved design that prevents the damage of such during evacuating and filling procedures.

12 Claims, 9 Drawing Sheets

PROPELLANT BAG IMPROVEMENT

BACKGROUND OF THE INVENTION

The present invention relates to an improved apparatus and method for filling the propellant chamber of an implantable pump. In particular, the present invention relates to an improved propellant bag or pillow for use in introducing propellant into the propellant chamber of an implantable pump, as well as methods of utilizing same.

Implantable pumps have been well known and widely utilized for many years. Typically, such devices are implanted into patients who require the delivery of active substances or medicaments to specific areas of their body. For instance, patients who are experiencing severe pain may require pain killers daily or multiple times per day. Absent the use of an implantable pump or the like, a patient of this type would be subjected to one or more painful injections of medication multiple times during the course of the day. In the case of pain associated with more remote areas of the body, such as the spine, these injections may be extremely difficult to administer and particularly painful for the patient. Moreover, attempting to treat conditions like these through oral or intravascular administration of medication often requires higher doses of medication that may cause severe side effects. Thus, it is widely recognized that utilizing an implantable pump may be beneficial to both the patient and the treating physician.

Many implantable pump designs have been proposed, including pumps employing mechanical means for and gas pressure driven propellant means for expelling fluids from the pump. The present invention is directly related to the latter. More particularly, the apparatus and methods taught in the present application are capable of being utilized with many different types of gas driven pumps, such as those shown in U.S. Pat. Nos. 4,969,873; 5,085,656; 5,336,194; 5,836,915; 5,722,957; 5,814,019; 5,766,150; and 6,730,060, as well as U.S. Patent Application Publication Nos. 2006/0259015, 2006/0259016, 2006/0271021, 2006/0271022, 2007/0005044, and 2007/0112328. The disclosures of each of the above-noted patents and patent applications are hereby incorporated by reference herein, and certain of these references may be referred to throughout the present application.

In general, gas driven implantable pumps, like each of the above-noted patents and patent applications, utilize an expandable propellant (e.g., an isobarically expanding gas) that acts upon a membrane to push medicament or other fluid from the pump. A common problem with such pumps, which have existed for some time, revolves around the filling of the propellant chamber with propellant. Above-noted U.S. Pat. No. 5,766,150 ("the '150 patent") discloses an apparatus and method for use in such a filling process. As is shown in FIG. 1 of the '150 patent (reprinted as FIG. 1 of the present case), that patent teaches the use of a propellant pillow 13, which is filled with a gas propellant and placed into a propellant chamber 7 of an implantable pump. The chamber is thereafter sealed. FIG. 2 shows pillow 13 in greater detail, in particular the fact that the pillow includes a propellant bag 15 and septum 17 affixed to the bag, which are not labeled as such in the '150 patent. Because bag 15 consists of a material through which the propellant may diffuse (i.e., a permeable material), the gas slowly diffuses through the wall of the pillow and into chamber 7. Thus, the use of pillow 13 allows time for the propellant chamber and the remainder of the pump to be assembled before the gas escapes therefrom.

During assembly of a pump utilizing the device and methods taught in the '150 patent, the assembly steps first include punching bag 15 from an air padded foil or the like, evacuating it of all gases, and subsequently refilling it with a propellant. These steps generally involve the use of at least one cannula, needle, or syringe 19 that pierces self-sealing silicone septum 17 to both evacuate all gases and introduce propellant. After being filled, pillow 13 is then introduced into a pump that has been divided into propellant chamber 7 and a fluid/medicament storage chamber 6. Subsequent to inserting pillow 13 into propellant chamber 7 of the pump, that chamber is sealed and evacuated of all gases. This allows the propellant to slowly permeate through the walls of bag 15 and into propellant chamber 7. This method is generally applicable to any gas pressurized implantable pump, including the ones described in the various prior art references listed above. It has also been found that when a heat procedure is utilized to seal a propellant chamber like chamber 7, bags like bag 15 are caused to erupt (with one or more holes), thereby causing the propellant to more quickly fill the chamber.

While the device and methods taught in the '150 patent has been utilized for some time in filling implantable pumps such as those disclosed above, it is not without its drawbacks. For instance, the initial evacuation of and subsequent filling of propellant within pillow 15 sometimes results in the structure of the bag being damaged by the syringe(s) 19. More particularly, evacuation of gas from bag 15 (i.e., creating a vacuum) causes the walls of the bag to collapse upon themselves and sometimes into contact with the point of the syringe(s). This may result in the walls being pierced, which thereby leads to a faster escape of the propellant from bag 15 than is desired. Thus, while the '150 patent suggests placing the pillow within a sealed propellant chamber in approximately two minutes, this time period is significantly reduced when the bag walls are damaged. More often than not, this damage to pillow 13 results in less propellant ultimately being contained within the propellant chamber.

Therefore, there exists a need for an improved pillow for use in an improved method of filling the propellant chamber of an implantable pump.

SUMMARY OF THE INVENTION

A first aspect of the present invention is a pillow for use in filling a gas pressure driven implantable pump. In a preferred embodiment, the pillow preferably includes a propellant bag for containing a propellant, the bag being formed of permeable material facilitating release of the propellant therefrom. The pillow also preferably includes a self-sealing septum structure having a top surface, a bottom surface, and a septum opening extending from the bottom surface partially through the septum structure. The bottom surface of the septum structure is preferably affixed to the bag.

In other embodiments according to the above-described first aspect, the septum structure includes two separate septa. In such a case, a first septum may include the bottom surface and the septum opening and a second septum is solid and includes the top surface. Other embodiments may include a bag that is unitary. The bag may also include a bag opening aligned with the septum opening. With regard to this latter embodiment, the bag opening may be formed subsequent to affixation of the septum structure to the bag. Still further embodiments employ a bag constructed of polyolefins, such as polypropylene or polyethylene, and a septum structure constructed of silicone rubber.

A second aspect of the present invention is a process for filling of a propellant chamber of a gas pressure driven implantable pump with a propellant. One preferred embodiment of this second aspect includes the steps of providing a pump having a medicament chamber and a propellant chamber, providing a propellant pillow including a permeable propellant bag and a self-sealing septum structure having a top surface, a bottom surface, and a septum opening extending from the bottom surface partially through the septum structure, the bottom surface being affixed to the bag, filling the pillow with the propellant, wherein the filling step includes laterally inserting a syringe into the septum structure, inserting the pillow filled with the propellant in the propellant chamber, and closing the propellant chamber.

Other embodiments of this second aspect may further include the step of evacuating the propellant chamber of substantially all gases. The evacuating step may be performed after the inserting step. The method may also include the step of evacuating the pillow of substantially all gases. The evacuating step may be performed through the use of the syringe inserted into said septum opening. Still further, the septum structure may include a first septum including the bottom surface and the septum opening and a second septum including the top surface. In such a case, the method may also include the steps of affixing the first septum to the bag and affixing the second septum to the first septum, through the use of an adhesive or the like.

A third aspect of the present invention is another pillow for use in filling a gas pressure driven implantable pump. In accordance with one preferred embodiment of this third aspect, the pillow includes a propellant bag for containing a propellant, the bag being formed of permeable material facilitating release of the propellant therefrom. The pillow may also include a first septum including a septum opening and a second septum being of a solid construction. The first septum is preferably affixed to the bag and the second septum is preferably affixed to the first septum.

In other embodiments of this third aspect, the bag is unitary. Likewise, the bag may include a bag opening aligned with the septum opening. Such an opening may be formed subsequent to affixation of the septum structure to the bag.

BRIEF DESCRIPTION OF THE DRAWINGS

A more complete appreciation of the subject matter of the present invention and the various advantages thereof can be realized by reference to the following detailed description in which references made to the accompanying drawings in which.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents which operate in a similar manner to accomplish a similar purpose.

Figure 1:
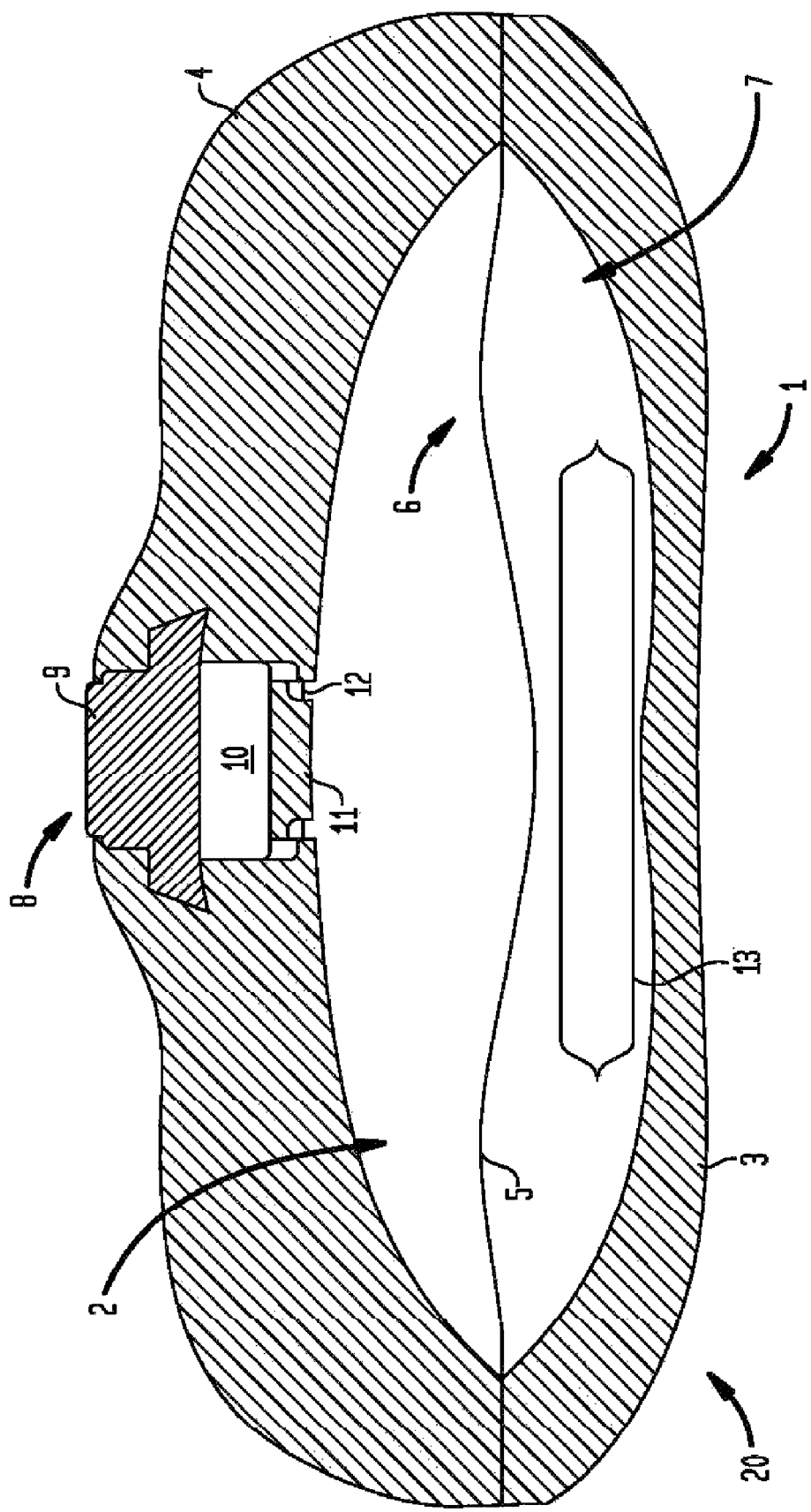
FIG. 1 is a cross-sectional side view of a prior art propellant pillow disposed within a propellant chamber of an implantable pump.
Figure 2:
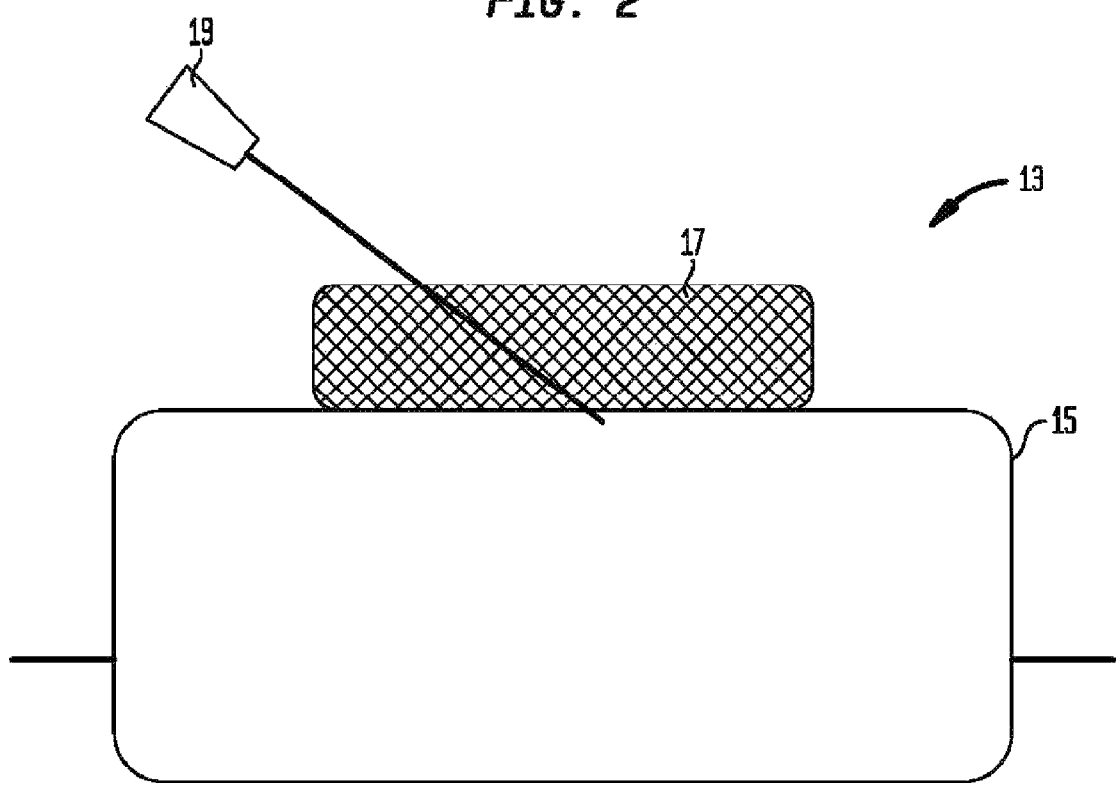
FIG. 2 is an enlarged cross-sectional illustration of the propellant pillow shown in FIG. 1 with a needle inserted therein.
Figure 3:
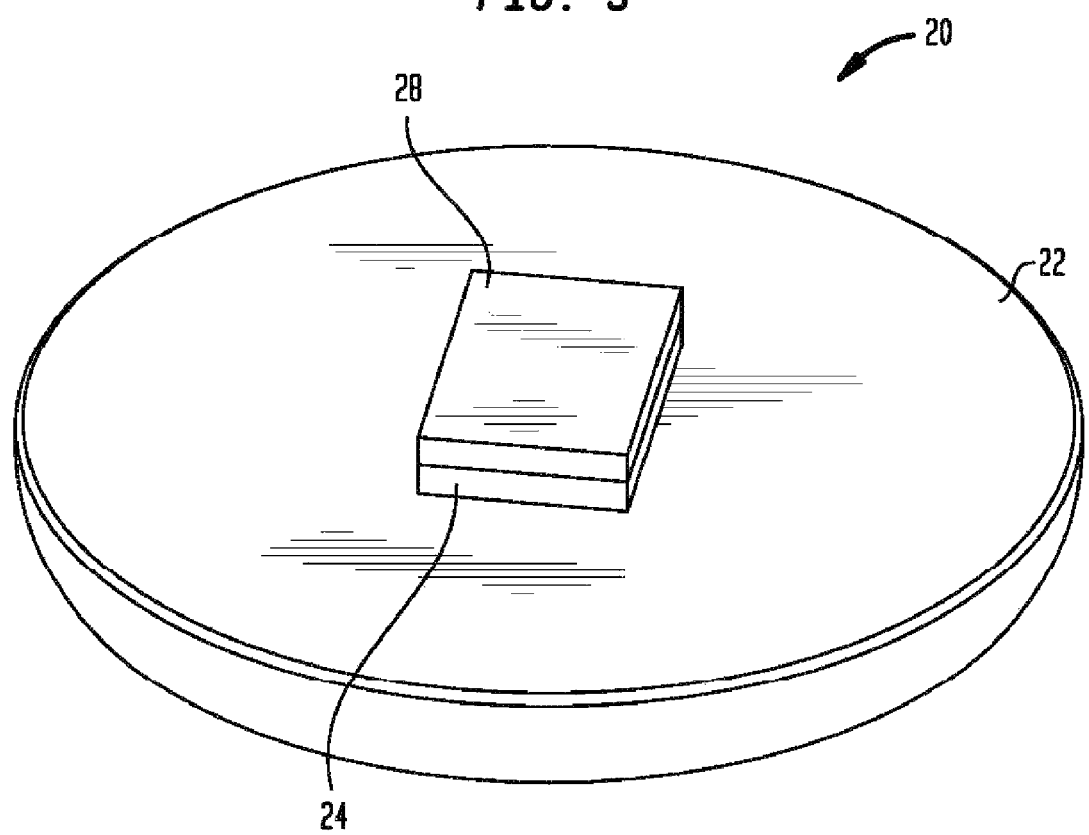
FIG. 3 is a perspective view of a propellant pillow in accordance with one embodiment of the present invention.
Figure 4:
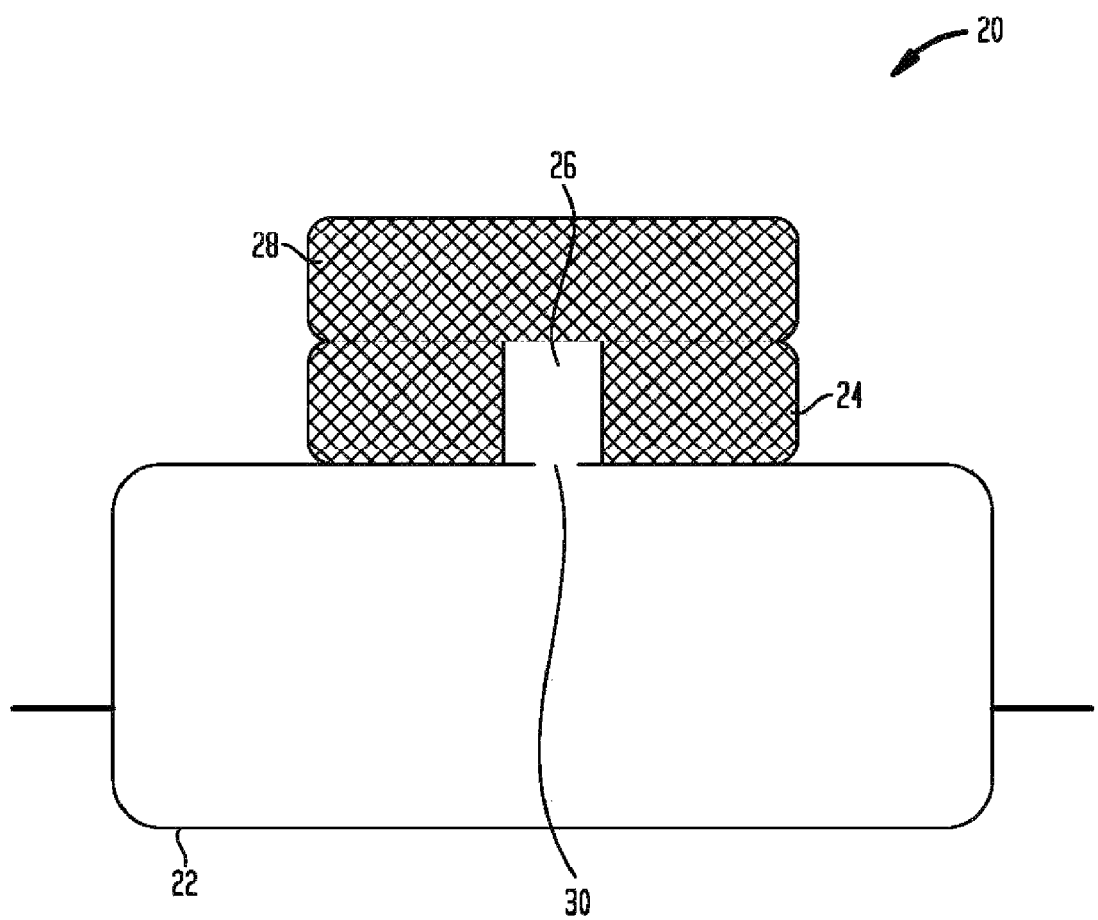
FIG. 4 is a cross-sectional side view of the propellant pillow shown in FIG. 3.

Referring to FIGS. 3 and 4, there is shown an improved propellant pillow 20 in accordance with the present invention. As shown in that figure, as well as those figures that follow, pillow 20 includes a propellant bag 22, a first septum 24 including an opening 26, and a second septum 28 overlying the first septum. Although shown in the figures as being of a circular shape, propellant pillow 20, as well as its components, may take on any shape suitable for use in placement in an implantable pump or the like.

Figure 5:
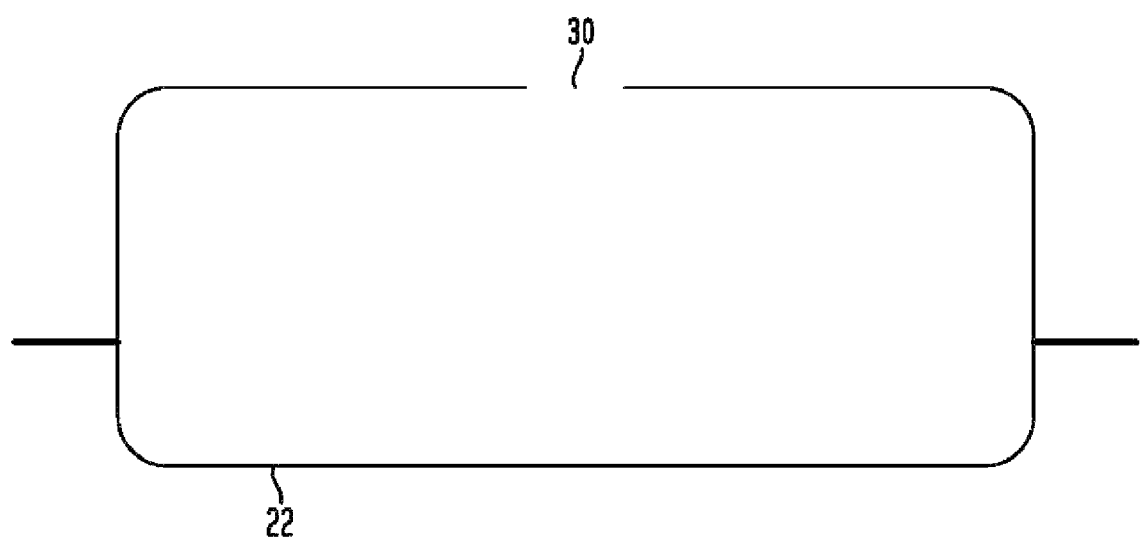
FIG. 5 is a cross-sectional side view of a propellant bag portion of the propellant pillow shown in FIG. 3 prior to assembly with other portions of the pillow.

Propellant bag 22 (shown by itself in FIG. 5) is preferably constructed of polyolefins, such as polypropylene or polyethylene, and, like in the '150 patent, is punched out from a larger sheet of similar bags. While the material is discussed above as being polypropylene or polyethylene, any material suitable for containing a propellant utilized in an implantable pump and thereafter allowing such to permeate through its walls can be used. In its initial state, propellant bag 22 is a completely sealed enclosure, but as will be discussed more fully below, at least one opening 30 is created in the propellant bag.

Figure 6:
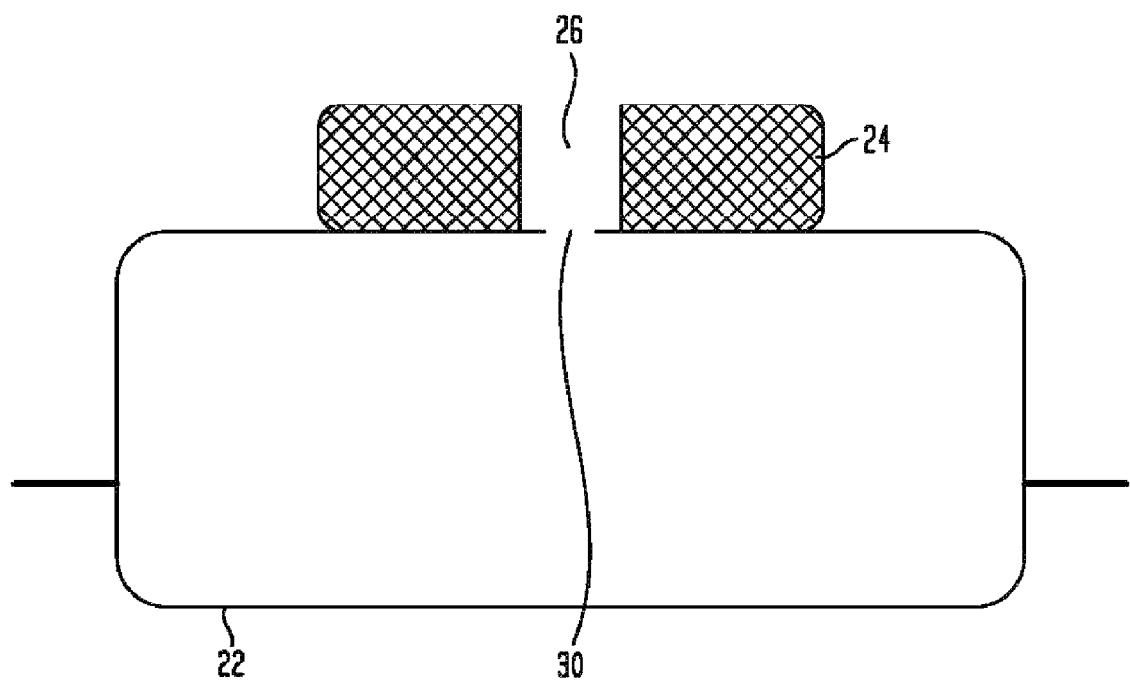
FIG. 6 is a cross-sectional side view of the propellant pillow of FIG. 3 with a first septum attached thereto.

Septa 24 and 28 are preferably created of silicone material, such as silicone rubber, but may be any material suitable for allowing resealing after the introduction of a needle therethrough. As is mentioned above, first or lower septum 24 is formed with opening 26 that allows for access to a portion of propellant bag 22. Overlying septum 24 is second or upper septum 28, which is a solid structure that not only overlies the first septum, but also opening 16. As shown in FIG. 6, first septum 24 is first affixed to propellant bag 22, with, second septum 28 thereafter being affixed to the first septum. Both of the septa are preferably affixed utilizing glue or other adhesive, such as cyanacrylate. However, other means of attaching these components to the propellant bag and each other may be utilized.

After septa 24 and 28 are placed on propellant bag 22, propellant pillow 20 is capable of being utilized to fill the propellant chamber of an implantable pump. Such a filling operation generally includes several steps. First, a syringe or other like device is inserted through septum 28 and opening 26 in first septum 24, and into contact with the portion of propellant bag 22 that opening 26 overlies (not shown). The introduction of the syringe creates opening 30 in propellant bag 22 at this location. Once opening 20 in propellant bag 22 is created, the syringe or needle is withdrawn. However, it is also contemplated to provide a propellant bag 22 which initially includes this opening prior to the application of septa 24 and 28 thereto. This is in fact shown in FIG. 5, and would negate the need for a separate opening forming step.

Figure 7:
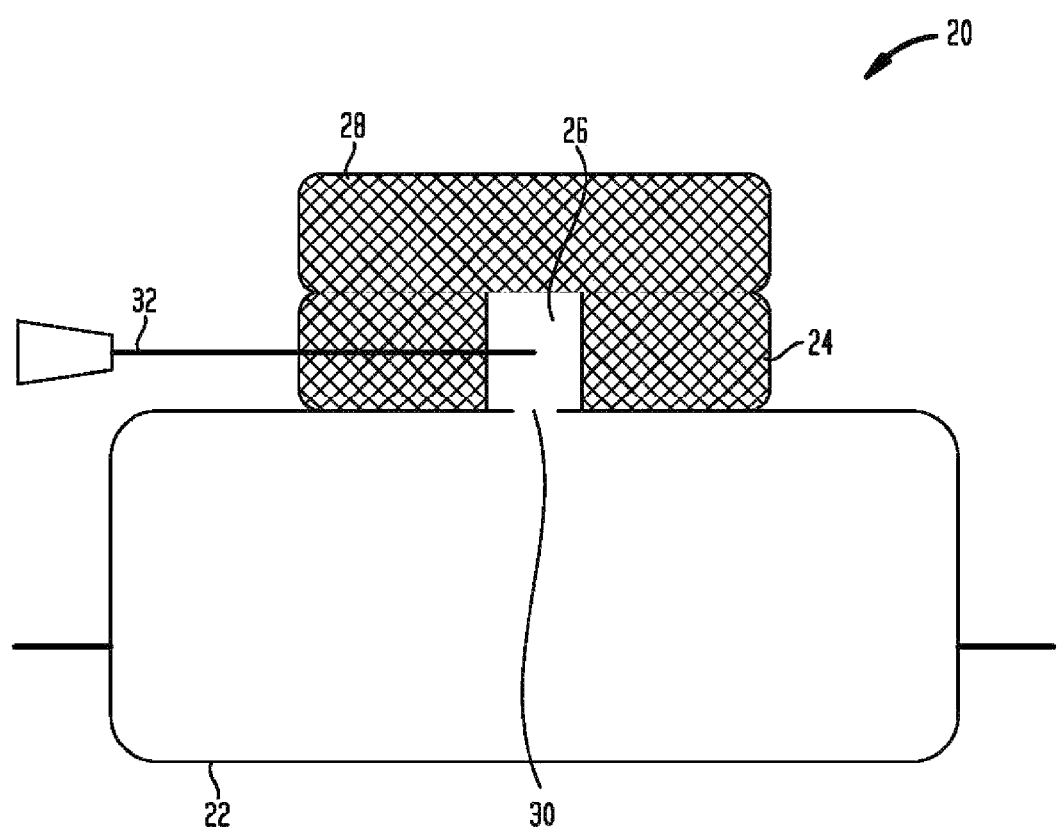
FIG. 7 is a cross-sectional side view of the propellant pillow of FIG. 3 illustrating the introduction of propellant into the propellant bag.

Second, the same or another needle or syringe 32 is inserted laterally through first septum 24 until the tip of the needle extends into opening 26 (best shown in FIG. 7). In this position, the needle can be utilized to evacuate all air or other gas that is contained within propellant bag 22, such that the air or other gas exits through opening 30 of propellant bag 22, into opening 26 of first septum 24, and through the needle.

Like in the prior art propellant pillows, this evacuation step generally results in propellant bag 22 collapsing upon itself. However, because of the design of the present propellant pillow, needle 32 is not permitted to engage any portion of propellant bag 22 during its collapse.

Figure 8:
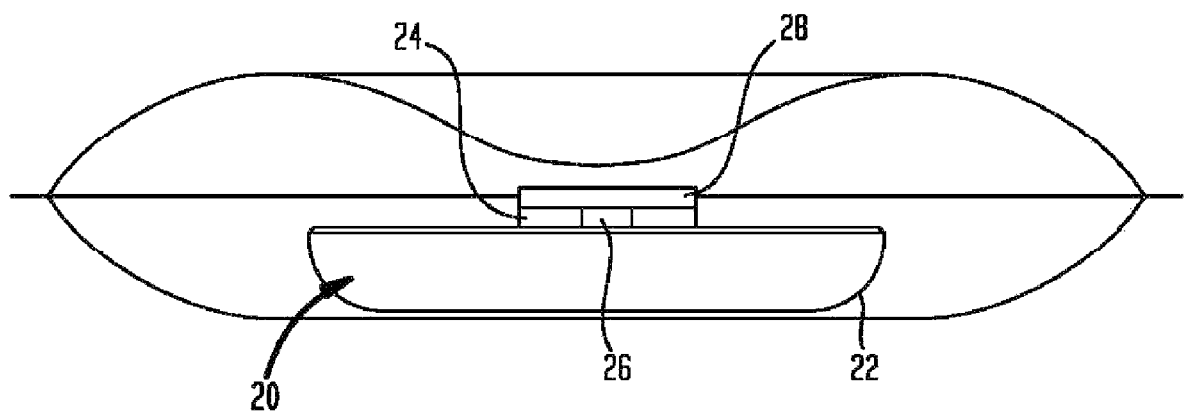
FIG. 8 is a cross-sectional side view illustrating the placement of the propellant pillow shown in FIG. 3 between two flexible membranes of an implantable pump.
Figure 9:
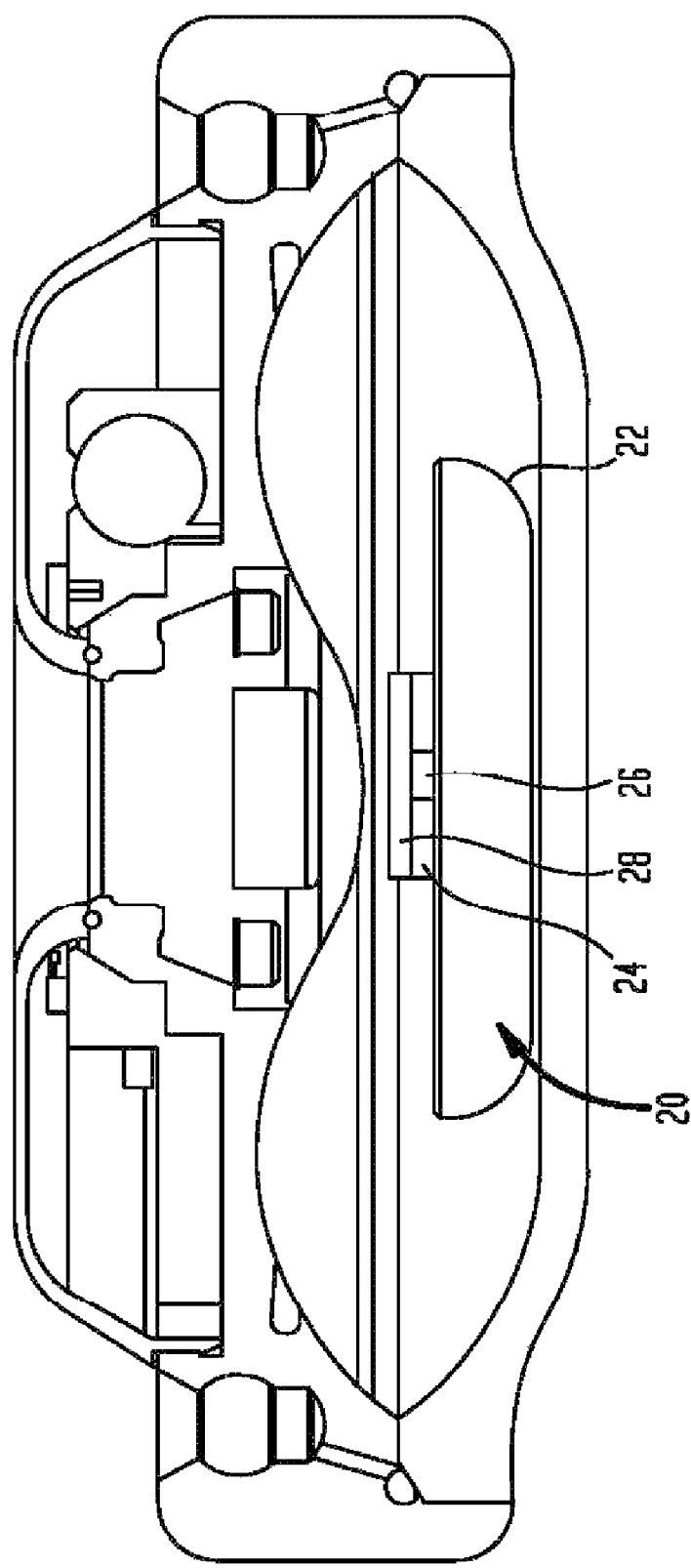
FIG. 9 is a cross-sectional side view of a fully assembled implantable pump with the propellant pillow of FIG. 3 placed within its propellant chamber.

Once the air or other gas has been evacuated from propellant bag 22, thereby creating a vacuum, the same laterally inserted syringe 32, or a subsequently inserted syringe, can be utilized to infuse propellant bag 22 with propellant. Again, any propellant exiting syringe 32 goes through opening 26 in first septum 24, through opening 30 of propellant bag 22, and into the propellant bag. After this filling step is completed, syringe 32 may be removed from first septum 24, which preferably self-seals because of its material. Propellant pillow 20 is now infused with gas that is only allowed to exit via a slow permeation through the material of propellant bag 22. The propellant pillow may then be placed in the propellant chamber of an implantable pump, much like is discussed in the '150 patent, and as is shown in FIGS. 8 and 9 of the present application. In particular, FIG. 8 shows propellant pillow 20 placed between two flexible membranes of an implantable pump, while FIG. 9 shows the propellant pillow placed in a fully assembled implantable pump. It is to be understood that like in the context of the '150 patent, the propellant chamber of the pump may be evacuated of all gas in order to create a vacuum. Further, this may be done before or after insertion of pillow 20 in the chamber. It is to be understood that other devices, like cannulas or needles, may be utilized in the foregoing steps.

It is contemplated that other designs for propellant pillow 20 may be employed. For instance, propellant bag 22 may, instead of being punched from a sheet of previously formed bags, be formed through the use of two membranes of like permeable material adjoined to one another. Likewise, it is contemplated that first and second septa 24 and 28 may in fact be integrally formed as a single septum. In this case, a lower surface of that single septum would include an opening corresponding to above-discussed opening 26. Finally, it is to be understood that the various embodiment propellant pillows 20 discussed herein, as well as the methods of utilizing same, can be utilized in conjunction with many different implantable pumps. Certain examples are provided in the present application, but these are by no means meant to limit the use of the propellant pillow to such disclosed pumps.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pillow for use in filling a gas pressure driven implantable pump comprising:
   a propellant bag for containing a propellant, the bag being formed of permeable material facilitating release of the propellant therefrom; and
   a self-sealing septum structure having a top surface, a bottom surface, a side surface and a septum opening extending from the bottom surface partially through the septum structure,
   wherein at least the side surface is resealable, the side surface includes a portion that, when punctured by a syringe, allows a portion of the syringe to extend into the septum opening, and the bottom surface is affixed to the bag.

2. The pillow of claim 1, wherein the septum structure includes two separate septa.

3. The pillow of claim 2, wherein a first septum includes the bottom surface and the septum opening and a second septum is solid and includes the top surface.

4. The pillow of claim 1, wherein the bag is unitary.

5. The pillow of claim 1, wherein the bag includes a bag opening aligned with the septum opening.

6. The pillow of claim 5, wherein the bag opening is formed subsequent to affixation of the septum structure to the bag.

7. The pillow of claim 1, wherein the bag is constructed of polypropylene or polyethylene.

8. The pillow of claim 1, wherein the septum structure is constructed of silicone rubber.

9. A pillow for use in filling a gas pressure driven implantable pump comprising:
   a propellant bag for containing a propellant, the bag being formed of permeable material facilitating release of the propellant therefrom;
   a first septum including a preformed septum opening; and
   a second septum being of a solid construction,
   wherein the first septum is affixed to the bag and the second septum is affixed to the first septum, and the first and second septa are resealable.

10. The pillow of claim 9, wherein the bag is unitary.

11. The pillow of claim 9, wherein the bag includes a bag opening aligned with the septum opening.

12. The pillow of claim 11, wherein the bag opening is formed subsequent to affixation of the septum structure to the bag.

* * * * *